United States Patent [19]

Schulz et al.

[11] 4,235,787

[45] Nov. 25, 1980

[54] BENZOPHENONE PENTACARBOXYLIC ACIDS AND THEIR DIANHYDRIDES

[75] Inventors: Johann G. D. Schulz, Pittsburgh; Anatoli Onopchenko, Monroeville, both of Pa.

[73] Assignee: Gulf Research & Development Company, Pittsburgh, Pa.

[21] Appl. No.: 101,919

[22] Filed: Dec. 10, 1979

[51] Int. Cl.³ .......................................... C07D 307/89
[52] U.S. Cl. ............................... 260/346.3; 562/410; 562/460
[58] Field of Search ......................... 260/346.3, 346.4; 562/460, 410

[56] References Cited

U.S. PATENT DOCUMENTS

| | | | |
|---|---|---|---|
| 2,548,982 | 4/1951 | Kemp | 260/649 R |
| 3,078,279 | 2/1963 | McCracken et al. | 260/346.4 |

OTHER PUBLICATIONS

Beilstein, vol. 10, p. 943.

*Primary Examiner*—Henry R. Jiles
*Assistant Examiner*—Bernard Dentz

[57] ABSTRACT

A novel isomeric mixture of benzophenone pentacarboxylic acids and their anhydrides.

9 Claims, No Drawings

BENZOPHENONE PENTACARBOXYLIC ACIDS AND THEIR DIANHYDRIDES

BACKGROUND OF THE INVENTION

1. Field of the Invention

This invention is directed to a novel isomeric mixture of benzophenone pentacarboxylic acids or their anhydrides.

2. Description of the Prior Art

U.S. Pat. No. 2,548,982 describes a process for the preparation of polyaryl polyparaffins. U.S. Pat. No. 3,078,279 to McCracken et al discloses the preparation of benzophenone tetracarboxylic dianhydrides.

SUMMARY OF THE INVENTION

We have discovered a novel isomeric mixture of benzophenone pentacarboxylic acids or their anhydrides containing the following specific structures:

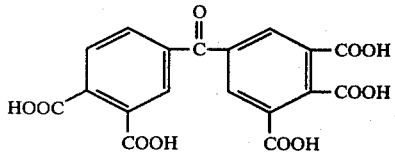

(3,4,5,3',4'-benzophenone pentacarboxylic acid),

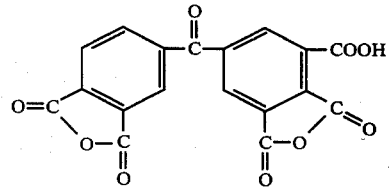

(5-carboxy-3,4,3',4'-benzophenone tetracarboxylic dianhydride),

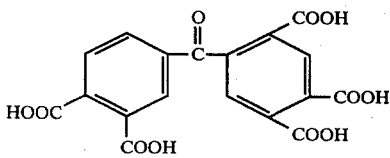

(3,2,4,5,3',4'-benzophenone pentacarboxylic acid),

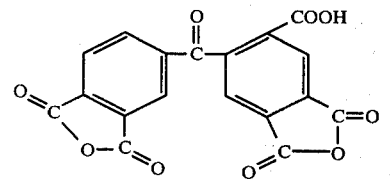

(2-carboxy-4,5,3',4'-benzophenone tetracarboxylic dianhydride),

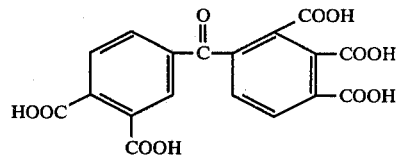

(2,3,4,3',4'-benzophenone pentacarboxylic acid)

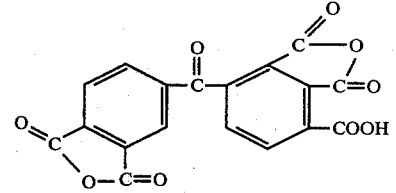

(4-carboxy-2,3,3',4'-benzophenone tetracarboxylic dianhydride) and

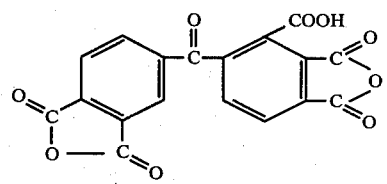

(2-carboxy-3,4,3',4'-benzophenone tetracarboxylic dianhydride).

To obtain the novel isomeric mixture of benzophenone pentacarboxylic acids or their dianhydrides claimed herein, an isomeric mixture of trixylyldiethanes is initially prepared as follows. One mol of acetaldehyde is dissolved in about one to about four mols of orthoxylene and added to about three to about six mols of a condensation agent, such as aqueous sulfuric acid having a concentration of about 90 to about 98 percent, over a period of about 15 to about 60 minutes while maintaining a temperature of about 10° to about 40° C. and preferably atmospheric pressure. The mixture is stirred for about five to about 60 minutes and then poured into an ice-water mixture. The organic layer is separated from the aqueous layer and distilled to recover unreacted ortho-xylene and 1,1-bis(3,4-dimethylphenyl)ethane. The residue is subjected to further distillation to recover an isomeric mixture of trixyldiethanes having a boiling point of about 230° C. at 1.4 mm of mercury containing largely the following specific trixyldiethanes:

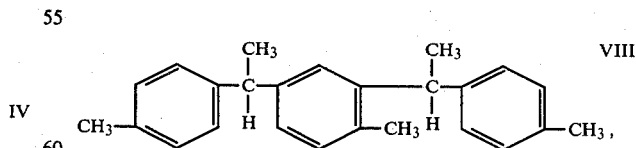

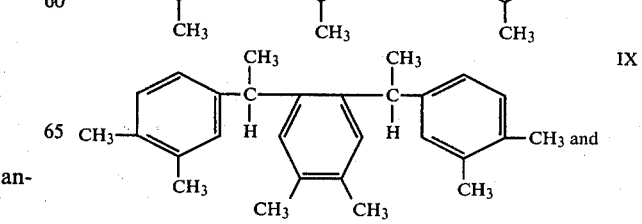

and

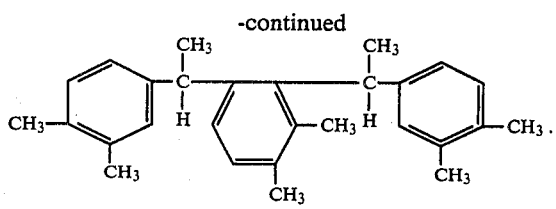

X

The isomeric mixture of trixylyldiethanes defined above is then subjected to oxidation with aqueous nitric acid having a concentration of about five to about 70 percent. The amount of nitric acid employed, determined as the molar ratio of 100 percent nitric acid relative to the charge, can be from about 10:1 to about 36:1. The reaction time needed for the reaction can be, for example, from about one minute to about 48 hours. Temperatures of about 110° to about 350° C. can be employed. Pressures sufficient to maintain the reaction system primarily in the liquid phase will suffice, for example from about atmospheric pressure (about one kilogram per square centimeter) to about 500 pounds per square inch gauge (about 35 kilograms per square centimeter). At the end of this period, the reaction mixture is permitted to come to ambient temperature and pressure and the residue can be evaporated to dryness. We expected to obtain a novel isomeric mixture of benzolybenzophenone hexacarboxylic acids containing the following specific benzoylbenzophenone hexacarboylic acids, in analogy to the benzophenone tetracarboxylic acid formation from nitric acid oxidation of 1,1-(3,4-dimethylphenyl)ethane (U.S. Pat. No. 3,078,279).

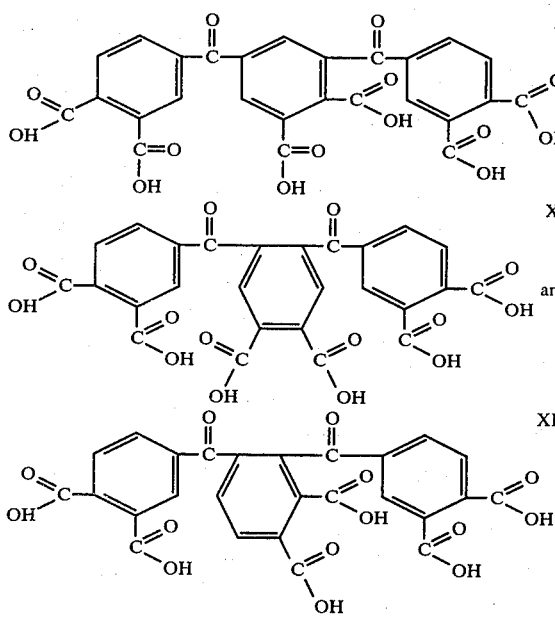

We were surprised, however, to find the product not to be a mixture of Compounds XI, XII and XIII but a mixture of benzophenone pentacarboxylic acids (Compounds I, III and V) instead.

In order to obtain the novel isomeric mixture of benzophenone pentacarboxylic dianhydrides claimed herein, the novel isomeric mixture of benzophenone pentacarboxylic acids (Compounds I, III and V) defined above is subjected to dehydration in a vacuum oven at a temperature of about 100° to about 300° C. for about one to about 48 hours. The resulting mixture will contain Compounds II, IV, VI and VII defined above.

DESCRIPTION OF PREFERRED EMBODIMENTS

The following discloses a procedure for obtaining the novel mixture of isomeric trixylyldiethanes. Into a five-liter, four-necked, round-bottomed flask equipped with a mechanical stirrer, a thermometer and two addition funnels, there was added 44 parts by weight (one mol) of acetaldehyde dissolved in 106 parts by weight (three mols) of orthoxylene and 294 parts by weight of concentrated sulfuric acid (three mols) over a period of 15 minutes. During the addition the temperature was maintained constant at 35° C. by application of external cooling and reaction was carried out at atmospheric pressure. After addition of reactants was completed, the mixture was stirred for an additional 10 minutes and then poured into the ice-water mixture. The organic layer was separated, washed twice with water and distilled to recover ortho-xylene, 130 parts by weight of 1,1-bis(3,4-dimethylphenyl)ethane (0.55 mol) and 31 parts by weight of a product having a boiling point range up to 270° C. at around 3.5 mm of mercury and 40 parts by weight of still higher-boiling residue. The fraction boiling up to 270° C. was redistilled to obtain the isomeric mixture of benzophenone pentacarboxylic acids (Compounds I, III and V) containing the individual compounds defined as Compounds VIII, IX and X hereinabove. The mixture was characterized as indicated below in Table I.

TABLE I

Boiling Point: 230° C. at 1.4 mm of Mercury
Expected Molecular Weight: 370.2660; Found: 370.2658
(Mass spec., m/e)

| Analysis | Weight Per Cent Carbon | Weight Per Cent Hydrogen |
|---|---|---|
| Calculated for $C_{28}H_{34}$: | 90.75 | 9.25 |
| Found | 90.85 | 9.18 |

NMR (CCl$_4$,TMS): 1.5 ppm (doublet, 6 protons, CH$_3$), 2.16 (singlet, 18 protons Aromatic CH$_3$), 4.2 (quartet, 2 protons, methine), and 6.87 (singlet, 8 protons, aromatic ring),
GLC: An isomeric mixture (three major peaks) corresponding to Compounds VIII, IX and X.

EXAMPLE II

The following discloses a procedure for obtaining the novel isomeric mixture of pentacarboxylic acids. About 37 grams of the mixture of isomeric trixylyldiethanes obtained in Example I (0.10 mol) were charged into a 700-milliliter, 316- stainless steel autoclave, together with 250 grams of water. The autoclave was brought to a temperature of 108°–110° C. and 150 milliliters of 70 percent aqueous nitric acid (2.3 mols) was added continuously over a period of 30 minutes. When addition of nitric acid was completed, the temperature was raised to 190° C. and the pressure controller was set to maintain a pressure of about 250 pounds per square inch gauge (17.6 kilograms per square centimeter) and held there for one hour. The autoclave was cooled and then depressured to ambient conditions and the product evaporated to dryness. The residue was washed several times with small amounts of water, filtered and dried in a vacuum oven to obtain 48.3 grams of a pale yellowish-green crystalline product consisting essentially of the novel mixture of isomeric benzophenone pentacarboxylic acids identified as Compounds I, III and V hereinabove. The mixture was characterized as indicated below in Table II.

TABLE II

| Analysis | Weight Per Cent Carbon | Weight Per Cent Hydrogen | Weight Per Cent Oxygen (by difference) |
|---|---|---|---|
| Calculated for $C_{18}H_{10}O_{11}$: | 53.74 | 2.51 | 43.75 |
| Found | 53.31 | 2.98 | 43.71 |
| Neutral Equivalent: | Theoretical 80.5; Found 90.9 | | |
| Molecular Weight: | Theoretical 402; Found 390 (Vapor Pressure Osmometry) | | |
| NMR (Acetone-$d_6$, TMS): | 6.55 (multiplet, aromatic ring protons) | | |
| Infrared (Nujol): | 1700 cm$^{-1}$, strong, COOH; 3700–3100 cm$^{-1}$ broad hydroxyl band of carboxylic acid; 1675 cm$^{-1}$; benzophenone carbonyl | | |
| GLC (as trimethylsilyl derivative, OV-1 column): 98 percent purity of benzophenone pentacarboxylic acids; emerge just past the benzophenone tetracarboxylic acid peak as a single broad peak. | | | |
| Transition Point: | 138° C. | | |
| Solubility: | water, acetone, methanol, chloroform, carbon tetrachloride and methyl ethyl ketone | | |

EXAMPLE III

About 40 grams of the novel mixture of isomeric pentacarboxylic acids obtained in Example II were subjected to dehydration in a vacuum oven at 140° to 145° C. for a period of 36 hours to obtain 35 grams of a yellowish product mixture. Dehydration was followed by infrared spectroscopy by the disappearance of 1700 cm$^{-1}$ band and the appearance of 1858 and 1781 cm$^{-1}$ anhydride bands. After dehydration was completed, a band at 1700 cm$^{-1}$ still persisted, indicating that some carboxyl groups, not convertible to anhydrides, were present. Ketone bands appeared at 1688 cm$^{-1}$. The product mixture, consisting essentially of Compounds II, IV, VI and VII, was characterized as indicated below in Table III. It should be kept in mind that with acids and/or anhydrides wherein a carboxyl group is located in the alpha position with respect to a benzophenone carbonyl, such as in Compounds III, IV, V and VIII, there may be some tendency for lactols to be formed; i.e.,

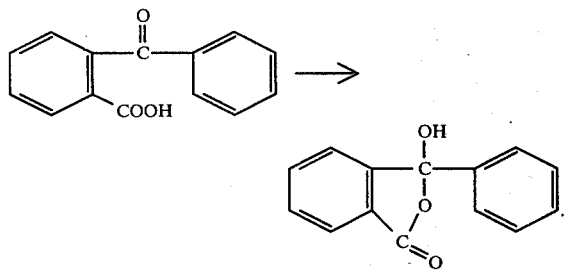

If such reaction had taken place with our mixture, neutral equivalent values of the order of 91–92 would have been expected. The values obtained therefore suggest that at least 89 percent (73.2/82.4) of our product is in the form of desired carboxyl dianhydrides.

TABLE III

| | | |
|---|---|---|
| Neutral Equivalent: | Theoretical 73.2; Found 82.4 | |
| Melting Point: | 125–130° C. | |

| Analysis: | Weight Percent Carbon | Weight Percent Hydrogen | Weight Percent Oxygen (by difference) |
|---|---|---|---|
| Calculated for $C_{18}H_6O_9$ | 59.03 | 1.65 | 39.32 |
| Found: | 58.33 | 1.65 | 40.00 |

EXAMPLE IV

In this example the dianhydride prepared above in Example III was reacted with a commercial epoxy resin (EPON-828) at 125° C. and atmospheric pressure, using a molar ratio of anhydride to epoxide of 0.60:1.0. The resulting resin, on cooling, gave an average Barcol hardness value of 31.0, using a Barcol Impressor 934-1, indicating that a crosslinked resin was formed, suitable for use as a coating for wires, metals, etc.

Obviously, many modifications and variations of the invention, as hereinabove set forth, can be made without departing from the spirit and scope thereof and only such limitations should be imposed as are indicated in the appended claims.

We claim:

1. An isomeric mixture of benzophenone pentacarboxylic acids containing the following compounds:
   (1) 3,4,5,3',4'=benzophenone pentacarboxylic acid,
   (2) 2,4,5,3,',4'-benzophenone pentacarboxylic acid and
   (3) 2,3,4,3',4'-benzophenone pentacarboxylic acid.

2. An isomeric mixture of benzophenone pentacarboxylic dianhydrides containing the following compounds:
   (1) 5-carboxy-3,4,3',4'-benzophenone tetracarboxylic dianhydride,
   (2) 2-carboxy-4,5,3',4'-benzophenone tetracarboxylic dianhydride,
   (3) 4-carboxy-2,3,3',4'-benzophenone tetracarboxylic dianhydride and
   (4) 2-carboxy-3,4,3',4'-benzophenone tetracarboxylic dianhydride.

3. 3,4,5,3',4'-benzophenone pentacarboxylic acid.
4. 2,4,5,3',4'-benzophenone pentacarboxylic acid.
5. 2,3,4,3',4'-benzophenone pentacarboxylic acid.
6. 5-carboxy-3,4,3',4'-benzophenone tetracarboxylic dianhydride.
7. 2-carboxy-4,5,3',4'-benzophenone tetracarboxylic dianhydride.
8. 4-carboxy-2,3,3',4'-benzophenone tetracarboxylic dianhydride.
9. 2-carboxy-3,4,3',4'-benzophenone tetracarboxylic dianhydride.

* * * * *